United States Patent [19]

Matay

[11] 4,134,302
[45] Jan. 16, 1979

[54] PULSER FOR ULTRASONIC INSPECTION SYSTEM

[75] Inventor: Istvan M. Matay, North Royalton, Ohio

[73] Assignee: TRW, Inc., Cleveland, Ohio

[21] Appl. No.: 869,276

[22] Filed: Jan. 13, 1978

[51] Int. Cl.² ............................................. G01N 29/04
[52] U.S. Cl. ........................................ 73/612; 73/642; 328/63
[58] Field of Search ................ 73/612, 642, 632, 627; 328/63; 331/172

[56] References Cited

U.S. PATENT DOCUMENTS

| 3,167,717 | 1/1965 | Jones et al. | 328/63 X |
| 3,982,425 | 9/1976 | McLain | 73/612 X |

Primary Examiner—Jerry W. Myracle

[57] ABSTRACT

A pulser circuit for providing electrical exciting pulses to a transducer in an ultrasonic testing apparatus in which a transducer transmits ultrasonic energy corresponding to the pulses into a test specimen. The pulser circuit includes a capacitor connected in series with a source of charging potential and a load impedance. A pair of switching transistors are connected in parallel and to the capacitor and the charging potential. A second switching transistor is connected directly across the capacitor. The first switching transistors turn on and cause the charged capacitor to develop the leading edge of a pulse across the load impedance. The leading edge turns on the second switching transistor which provides a direct discharge path for the capacitor and thereby shapes the pulse. Diode means is connected across the load impedance to assist in rapid recharging of the capacitor. The diode means is forward biased to provide a clamped reference potential for the pulse.

6 Claims, 2 Drawing Figures

PULSER FOR ULTRASONIC INSPECTION SYSTEM

GOVERNMENT CONTRACT

The invention herein described was made in the course of or under a contract or subcontract thereunder with the United States Air Force.

BACKGROUND OF THE INVENTION

This invention relates to ultrasonic nondestructive testing and more particularly to a pulser circuit for defining interrogating pulses employed in such testing.

Ultrasonic nondestructive evaluation techniques are based on transmission and reflection of acoustic energy in a material under test. Defects in the material are located and evaluated by the characteristics of the energy reflected from them. Examples of systems employing ultrasonic evaluation techniques are shown in U.S. Pat. Nos. 3,690,153, 3,981,184 and 4,004,454. In such systems the interrogating acoustic energy is provided from an electromechanical transducer to a material specimen in the form of pulses. The transducer receives electrical signals from a pulse generator or "pulser" and converts them to acoustic energy.

In many material inspection situations an increased spatial resolution is desirable along the direction of sound propagation in the material. A common limitation in such situations is the duration of the interrogating acoustic pulse. A long pulse creates an uninspectable "dead band" at each interface or discontinuity in the material from which the pulse is reflected. Increased spatial resolution requirements for certain materials and especially for such advanced material systems as composites, powder metallurgy and ceramics require a narrow interrogating acoustic pulse.

SUMMARY OF THE INVENTION

According to the present invention, there is provided an ultrasonic pulser circuit for supplying to an acoustic transducer exciting pulses having a high amplitude, narrow duration and short rise and fall times.

A pulser circuit embodying the present invention includes a capacitor and circuit means connecting the capacitor in charging relationship with a source of charging potential. A load impedance is connected in series with the capacitor and the charging potential. A first switch means having a substantially open first state and a substantially closed second state is connected to the capacitor. The first switch means causes the capacitor to develop the leading edge of a pulse across the load impedance upon switching from the first to the second state. A second switching means is connected across the capacitor and has a substantially open first state and a substantially closed second state. The second switch means is switched from the first to the second state by the pulse leading edge to provide a direct discharge path for the capacitor and thereby shape the pulse.

Preferably, the first switch means includes a pair of transistors connected in parallel and in parallel with both the capacitor and the source of charging potential. The parallel transistors provide both low switch resistance and low switching time so that a pulse of short rise time and high amplitude is developed across the load impedance.

The second switching means preferably includes a transistor having its collector to emitter path connected across the capacitor. The base of the transistor is connected so that the base to emitter junction is forward biased by the leading edge of the pulse.

The load impedance may include diode means to provide a path for rapidly charging the capacitor. Preferably, means is provided for forward biasing the diode means to establish a reference potential for the pulse.

DESCRIPTION OF A PREFERRED EMBODIMENT

Figure 1:
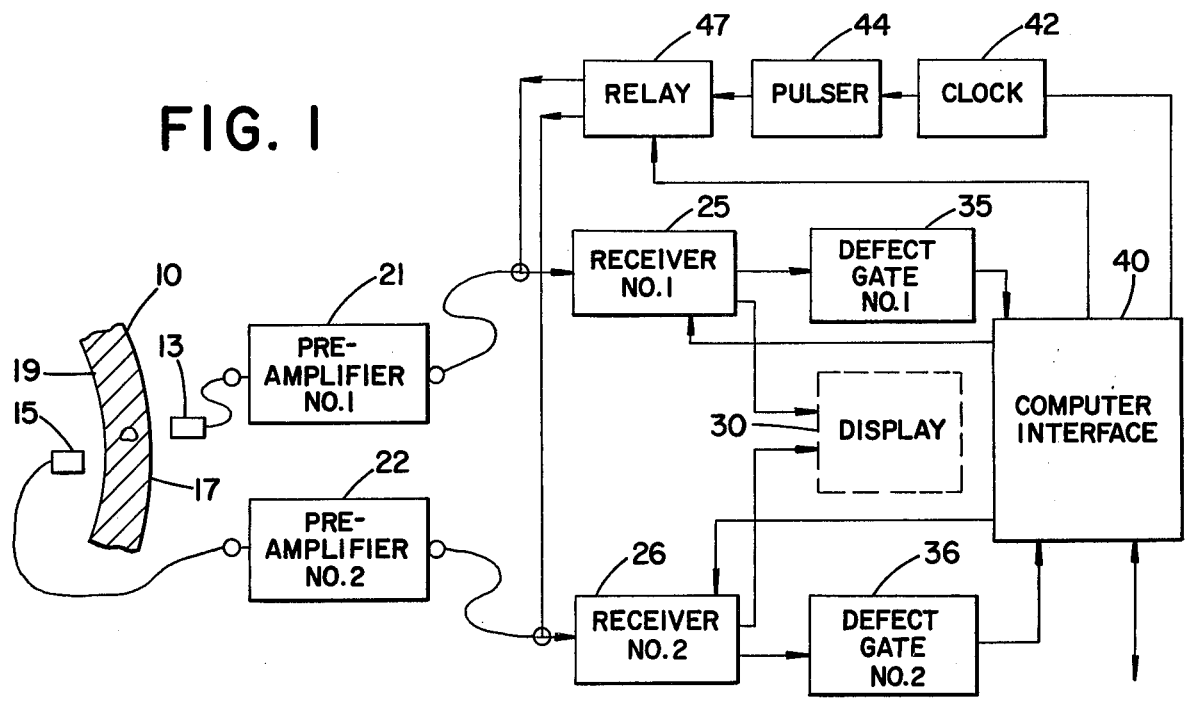
FIG. 1 is a block diagram of an ultrasonic inspection system in which a pulser embodying the present invention may be utilized.

There is shown in FIG. 1 an ultrasonic inspection system for inspecting a specimen 10 which may be, for example, a turbine disc. An ultrasonic interrogating pulse is applied periodically to the specimen 10 through a piezoelectric transducer 13 on one side of the specimen 10 or through a like tranducer 15 on the opposite side of the specimen. The pulse passes through specimen 10 from the front interface 17 to the rear interface 19 and is reflected from various discontinuities in the specimen. The pulse reflections may represent defects in the specimen or may represent "valid" discontinuities such as the front and rear interfaces. The front interface 17 and rear interface 19 have been identified with respect to transducer 13. It will be appreciated that the two interfaces would be interchanged from the point of view of transducer 15.

Each reflected pulse passes through either transducer 13 or 15 and respective preamplifier 21 or 22 to a receiver 25 or 26. Each receiver applies its output to a display unit 30 and also to a defect gate 35 or 36. Each defect gate 35, 36 operates to detect the potential specimen defect indications in its receiver output signal within predetermined depth boundaries in the specimen. Each gate acquires the amplitude and location data for specimen defects within the gate bounds and supplies such information to a computer (not shown) through a computer interface 40.

Pulses are supplied to transducers 13 and 15 at intervals determined by a pulser clock 42 which at the selected intervals supplies a triggering pulse to a pulser 44. Each pulse is directed under control of the computer through interface 40 or by manual selection through relay 47 to one or the other of transducers 13 and 15. The rate at which triggering pulses are supplied from pulser clock 42 may be selected by an appropriate manual switch or under control of the computer through the computer interface 40.

Figure 2:
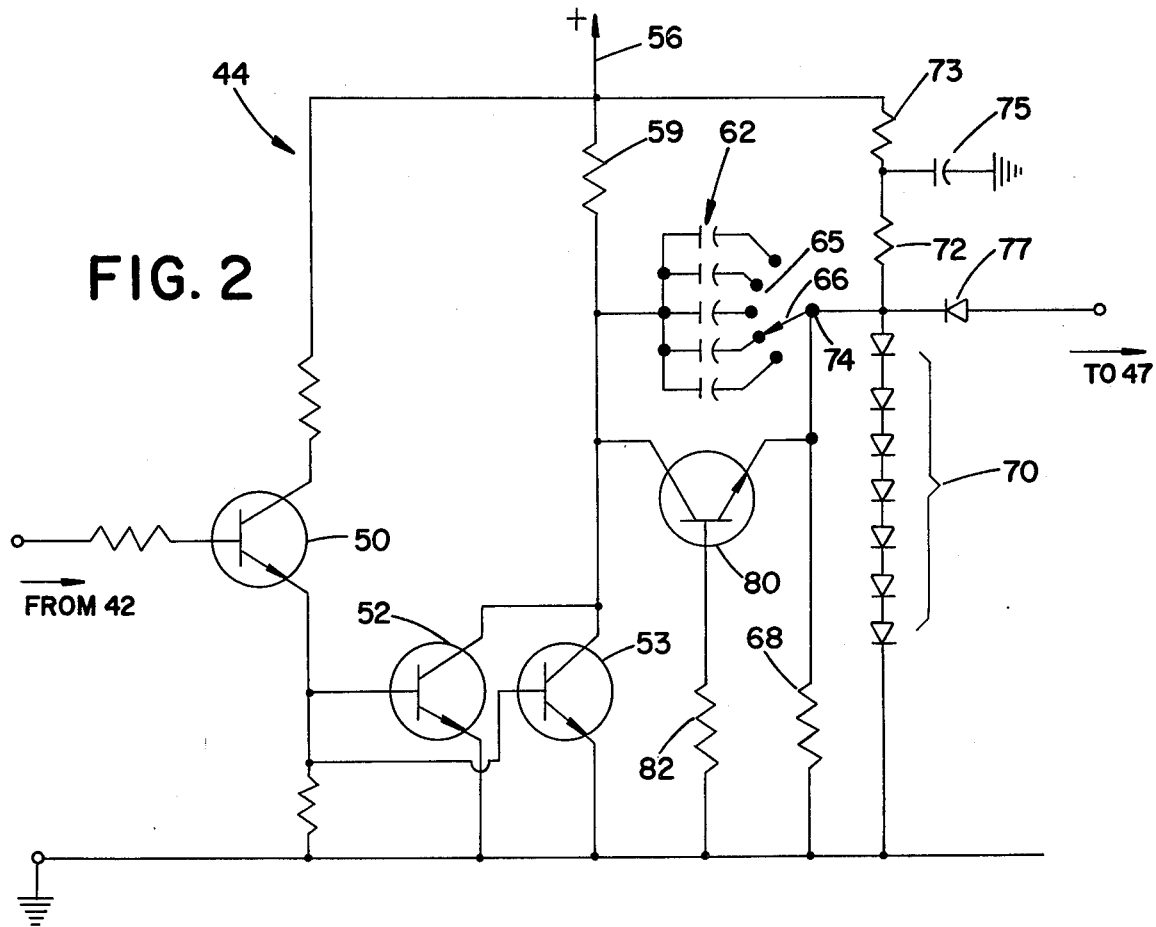
FIG. 2 is a schematic diagram of a pulser circuit embodying the present invention.

There is shown in FIG. 2 a pulse forming circuit for the pulser 44 which is capable of supplying to a piezoelectric acoustic transducer pulses having the desirable characteristics of high amplitude, short duration and fast rise and fall times. The circuit is capable of supplying such pulses through a relatively long connecting cable to the transducer and at high repetition rates.

As shown in FIG. 2, the circuit includes a driver transistor 50 which receives triggering pulses from the pulser clock 42. The triggering pulses establish the pulse repetition rate of the pulser circuit. The emitter of driver transistor 50 is connected to the bases of a pair of parallel switching transistors 52 and 53. These transistors are selected for high voltage operation and for having high current gain/bandwidth product. The collectors of transistors 52 and 53 are connected together and to a high voltage power supply 56 through a load resistor 59. The emitter of each transistor is connected to ground.

A bank of capacitors generally designated 62 has one terminal of each capacitor connected in common to the collectors of switching transistors 52 and 53. The remaining terminal of each capacitor in the bank 62 is connected to a terminal of a selector switch 65. The capacitor bank 62 provides a selection of capacitors having capacitance values which determine the duration of the output pulse. A particular capacitor is selected, therefore, according to the duration of the pulse desired for the particular application by means of selector switch 65. The movable selector arm 66 of switch 65 is connected to a load resistor 68.

A diode string generally designated 70 is connected across load resistor 68. A pair of resistors 72 and 73 are connected between high voltage power supply 56 and the anode of diode string 70. The diodes provide a low resistance charging path for the selected capacitor in bank 62 while the resistors 72 and 73 provide a path to forward bias the diodes and clamp point 74 slightly above ground potential. A string of diodes is used to increase the peak inverse voltage rating.

A capacitor 75 is connected from the junction of resistors 72 and 73 to ground and serves to compensate for the capacitance associated with the diode string 70. A diode 77 has its cathode connected to point 74 and its anode connected to relay 47 (FIG. 1). Diode 77 is normally reverse biased and decouples point 74 from the transducers 13 or 15.

A switching transistor 80 has its collector connected to the collectors of switching transistors 52 and 53 and its emitter connected to the movable arm 66 of selector switch 65. The collector to emitter path of transistor 80 is thus directly across the capacitor of bank 62 which is selected by selector switch 65. The base of transistor 80 is connected to ground through resistor 82. Transistor 80 is selected for the same characteristics as switching transistors 52 and 53 and preferably is of the same type.

In operation, driver transistor 50 and switching transistors 52, 53 and 80 are nonconductive until a triggering pulse is received from pulser clock 42. The selected capacitor in bank 62 is charged to the potential of high voltage supply 56 through resistor 59 and diode string 70. Point 74 is clamped to a voltage level slightly above ground. Upon receipt of a triggering pulse from pulser clock 42 driver transistor 50 becomes conductive and turns on switching transistors 52 and 53. When transistors 52 and 53 are switched on the positively charged terminal of the selected capacitor is connected to ground through the very low internal resistances of switching transistors 52 and 53. Point 74 at the opposite terminal of the selected capacitor is driven sharply negative. The leading edge of a negative pulse having an amplitude substantially equal to the value of the supply voltage 56 is thereby developed across load resistor 68 and diode string 70.

This negative edge causes the base to emitter junction of transistor 80 to become forward biased so that the transistor is turned on and provides a very low resistance discharge path for the selected capacitor. The selected capacitor, therefore, discharges rapidly through transistor 80 and the voltage level of point 74 is restored to substantially its former level. The output pulse formed is transmitted through diode 77 to the selected transducer.

At the end of the triggering pulse from pulser clock 42 driver transistor 50 and switching transistors 52 and 53 are turned off and the selected capacitor begins to recharge. Because point 74 is clamped to a level near ground no output pulse appears when the capacitor recharges.

In a particular example of the pulsing circuit, the capacitors in capacitor bank 62 were selected to provide a pulse duration corresponding to a half wave of 1.0, 2.25, 5.0, 10.0 and 15.0 MHz frequencies. The remaining components were as follows:

| | |
|---|---|
| Transistors 52, 53, and 80 | 2N5657 |
| Transistor 50 | 2N2222 |
| Diodes 70 | 1N4148 |
| Diode 77 | 1N4001 |
| High Voltage Supply 56 | +50 to 500 volts, adjustable |
| Resistor 59 | 110,000 ohms |
| Resistor 68 | 5000 ohms |
| Resistor 82 | 100 ohms |
| Resistor 72 | 15,000 ohms |
| Resistor 73 | 33 ohms |
| Capacitor 75 | 1000 picofarads |

What is claimed is:

1. In an ultrasonic testing apparatus in which a transducer receives electrical exciting pulses and transmits ultrasonic energy corresponding thereto into a test specimen, a pulser circuit for forming said exciting pulses comprising a capacitor, circuit means connecting said capacitor in charging relationship with source of charging potential, a load impedance connected in series with said capacitor and said charging potential, first switch means having a substantially open first state and a substantially closed second state, said first switching means being connected to said capacitor for causing said capacitor to develop the leading edge of a pulse across said load impedance upon switching from said first to said second state, and second switching means connected across said capacitor and having a substantially open first state and a substantially closed second state, said second switching means being switched from said first to said second state by said leading edge to thereby shape said pulse.

2. A pulser circuit as claimed in claim 1 wherein said first switch means comprises a pair of transistors connected in parallel and in parallel with both said capacitor and said source of charging potential.

3. A pulser circuit as claimed in claim 1 wherein said second switching means comprises a transistor having its collector to emitter path connected across said capacitor, the base to emitter junction of said transistor being forward biased by said leading edge to render said transistor conductive to rapidly discharge said capacitor.

4. A pulser circuit as claimed in claim 1 wherein said load impedance includes diode means to provide a path for rapidly charging said capacitor when said first switch means is in said first state.

5. A pulser circuit as claimed in claim 4 further comprising means for forward biasing said diode means to establish a reference potential for said pulse.

6. For use in an ultrasonic testing apparatus in which a transducer receives electrical exciting pulses and transmits ultrasonic energy corresponding thereto into a test specimen, a pulser circuit for forming said exciting pulses comprising a capacitor, first switching means for substantially instantaneously changing the voltage applied on one side of said capacitor to develop a sharp voltage swing on the other side of said capacitor, second switching means connected across said capacitor for providing a discharge path for said capacitor independent of said first switching means and actuated in response to said sharp voltage swing to provide a low impedance discharge path for substantially discharging said capacitor in a time period essentially determined by the capacitance of said capacitor, and output means connected to said other side of said capacitor to provide an output pulse in response to said voltage swing and the discharging of said capacitor.

* * * * *